United States Patent [19]

Smith et al.

[11] 4,421,936
[45] Dec. 20, 1983

[54] CONTINUOUS ALKOXIDATION PROCESS

[75] Inventors: Harry M. Smith, St. Albans; Raymond D. Williams, Eleanor, both of W. Va.

[73] Assignee: FMC Corporation, Philadelphia, Pa.

[21] Appl. No.: 480,977

[22] Filed: Mar. 31, 1983

Related U.S. Application Data

[63] Continuation-in-part of Ser. No. 366,262, Apr. 7, 1982, abandoned.

[51] Int. Cl.³ .................. C07C 29/70; C07C 43/13
[52] U.S. Cl. ................................. 568/678; 260/933; 568/851
[58] Field of Search ................................ 568/851, 678

[56] References Cited

U.S. PATENT DOCUMENTS 1,910,331 5/1933 Halbig ............................... 568/851
2,877,274 3/1959 Kramis ............................. 568/851

FOREIGN PATENT DOCUMENTS 490388 8/1938 United Kingdom ............... 568/851
698282 10/1953 United Kingdom ............... 568/851

OTHER PUBLICATIONS

Turova et al., "Russian Chemical Reviews", Mar. 1965, pp. 161–185.

Primary Examiner—J. E. Evans
Attorney, Agent, or Firm—Charles C. Fellows; Eugene G. Horsky

[57] ABSTRACT

A continuous process for producing alkali metal alkoxides comprising continuously introducing an aqueous solution of an alkali metal hydroxide into an upper section of a column reactor; continuously vaporizing an alkanol or an alkoxyalkanol of 4 to 18 carbon atoms into a lower section of the reactor at a rate of at least about 2 to 4 moles of alcohol for each mole of alkali metal hydroxide introduced into the reaction zone; reacting the aliphatic alcohol with the alkali metal hydroxide in the reactor; concurrently removing water from the alkali metal hydroxide solution and the alkoxide formation from an upper section of the reactor as an azeotrope formed by excess alcohol and water; continuously condensing and separating the azeotrope into an alcohol phase and a water phase, the water phase being removed from the process and the alcohol phase being returned to the column reactor; and removing a substantially anhydrous reaction product consisting primarily of alkoxide product in excess alcohol from a bottom section of the reactor while simultaneously maintaining a nonoxidizing atmosphere while conducting the reaction.

6 Claims, 1 Drawing Figure

CO-PRODUCT CONTINUOUS ALKOXIDE PROCESS

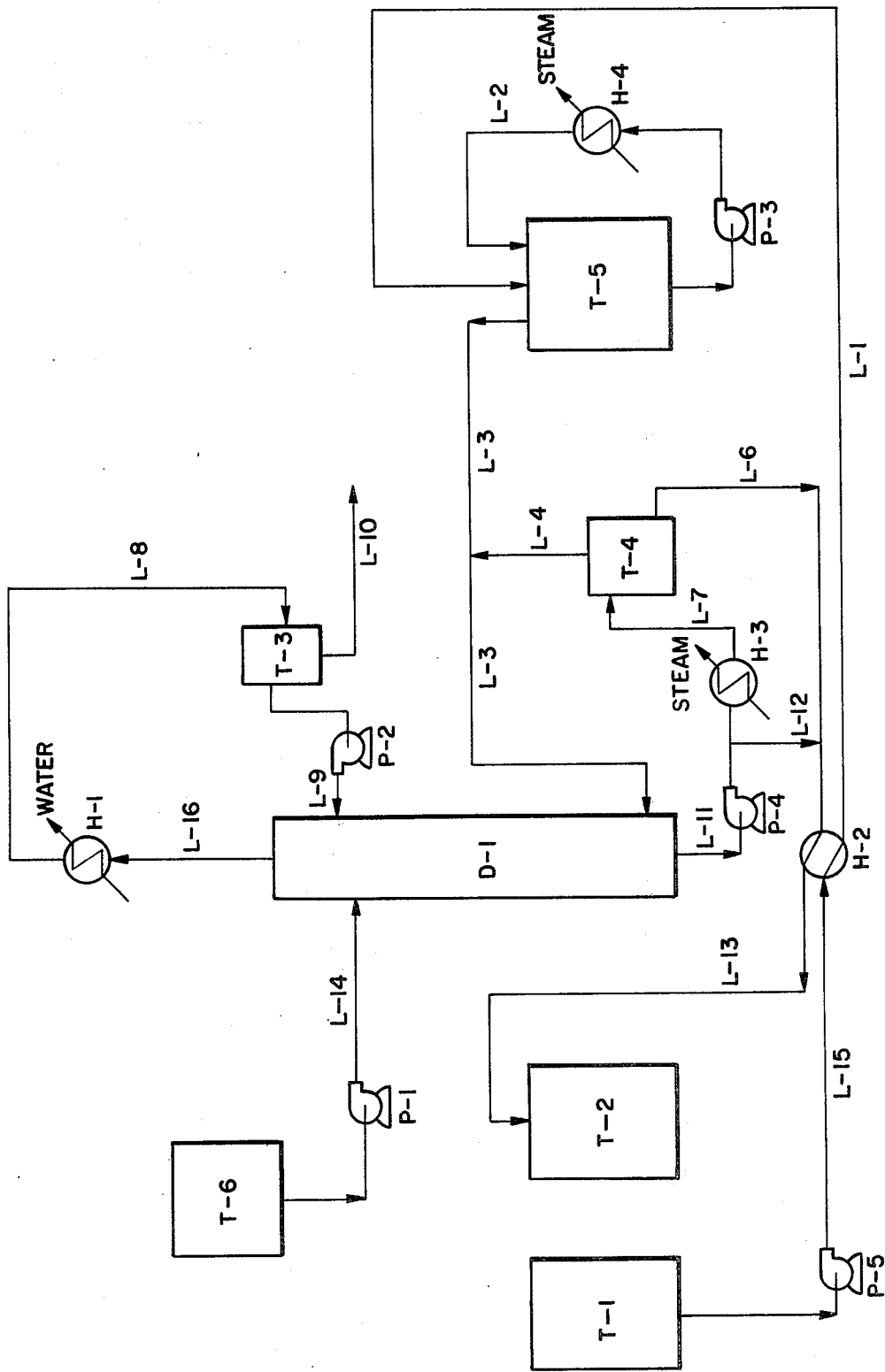

CONTINUOUS ALKOXIDATION PROCESS

This application is a continuation in part of U.S. Ser. No. 366,262 filed Apr. 7, 1982 now abandoned.

This invention relates to a continuous process for producing alkali metal alkoxides by continuously reacting an aliphatic alcohol and an alkali metal hydroxide while concurrently removing substantially all the water formed in the process.

The production of alkyl and alkoxyalkyl phosphates such as trialkyl phosphate and trialkoxy alkyl phosphates are generally made in batch processes on a relatively small scale. It is convenient when making related compounds such as tributyl phosphate and tributoxyethyl phosphate to make the corresponding alkoxides such as sodium butoxide and sodium 2-butoxyethoxide batchwise in the same equipment in alternate production runs. Sodium 2-butoxyethoxide can be produced by reacting sodium hydroxide and 2-butoxyethanol in a reactor and azeotropically removing the water through a distillation column. Sodium butoxide is similarly produced except that N-butyl alcohol is used in place of 2-butoxyethanol. The production of these alkoxides or alkali metal alcoholates are described in detail in U.S. Pat. No. 3,020,303.

Alkoxides, for use in producing phosphate esters, are typically produced as 20 to 30% by weight solutions of alkoxide in alcohol, for example, butoxide in butanol or 2-butoxyethoxide in 2-butoxyethanol. In producing phosphate esters, the excess alcohol from the alkoxidation reaction is present during the phosphorylation reaction. After phosphorylation, the reaction mixture is washed with water to stop the reaction and remove sodium chloride. The wet alcohol is separated from the water and phosphate ester, then the alcohol is dried and returned to the alkoxidation section of the phosphate ester plant. A non-oxidizing atmosphere is employed during both the alkoxidation and phosphorylation reactions to minimize development of color in the phosphate esters.

Color specifications for commercial grade phosphate esters are high; e.g., the maximum color for tributyl phosphate is 50 and 150 for tributoxyethyl phosphate determined according to ASTM test method D 1209-69 (Reapproved 1974) Color of Clear Liquids (Platinum-Cobalt Scale). Discoloration of the phosphate ester is undesirable as this reduces the value of the ester. Nevertheless from time to time high color esters, some nearly black, are produced.

The present invention provides a continuous process for producing alkali metal alkoxides comprising the steps:

(a) Continuously introducing an aqueous solution of an alkali metal hydroxide into an upper section of a reaction zone;

(b) Continuously vaporizing an aliphatic alcohol of the formula

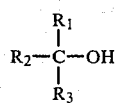

$R_1$, $R_2$ and $R_3$ being selected from the group consisting of hydrogen or alkyl and alkoxyalkyl radicals having from 4 to 18 carbon atoms into a lower section of the reaction zone at a rate of at least about 2 to 4 moles of alcohol for each mole of alkali metal hydroxide introduced into the reaction zone;

(c) reacting the aliphatic alcohol with the alkali metal hydroxide in the reaction zone;

(d) concurrently removing water from the alkali metal hydroxide solution and the alkoxide formation from an upper section of the reaction zone as an azeotrope formed by excess alcohol and water;

(e) removing a substantially anhydrous reaction product consisting primarily of alkoxide product in excess alcohol from a bottom section of the reaction zone while simultaneously maintaining a nonoxidizing atmosphere throughout the conduct of steps a through e.

The preferred method of operation of the processes utilizes a reaction zone that can be termed a dehydration column reactor which is used as a reactor and for substantially dehydrating the reaction mixture before it leaves the column. In this method of operation, the alkali metal hydroxide is introduced to the column near its top. Vaporized alcohol in excess of the amount that can react with the hydroxide is fed to the column near the bottom of the column. The top section of the column is configured so water distilled overhead as an azeotrope formed with some of the excess alcohol is removed from the top of the column and the azeotrope is condensed and separated into an alcohol phase and an aqueous phase. The aqueous phase is removed from the process and the condensed alcohol phase is returned to the column. The reaction mixture removed from the bottom of the column contains the alkoxide product and excess alcohol, i.e. alcohol not reacted with the alkali metal hydroxide. The reaction mixture can be stored or used directly in making other product. For example, it can be phosphorylated with phosphorus oxichloride to make a triorganic phosphate. Optionally, part of the excess alcohol can be removed from the reaction mixture and recycled to the process before the reaction product is used in making another product or stored for later use.

Aliphatic alcohols useful in the present process include those having the formula

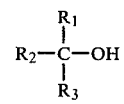

in which $R_1$, $R_2$, and $R_3$ are hydrogen, alkyl or alkoxyalkyl radicals having 4 to 18 carbon atoms. The alcohols include alkanols such as n-butanol, s-butanol, amyl alcohol, 2-ethylhexanol, octanol, n-dodecanol and octadecanol and alkoxyalkyl substituted carbinols of the formula $R_4$—O—$R_5$—OH in which $R_4$ contains 1 to 6 carbon atoms and $R_5$ contains 1 to 4 carbon atoms and include carbinols such as 2-methoxyethanol, 2-ethoxyethanol, 2-butoxyethanol, 2-i-propoxyethanol and 2-ethoxyethanol, which latter mixed carbinols have chain lengths ranging from 2 to 18 carbon atoms.

The alcohols are employed in amounts of at least about 2-4 moles per mole of aqueous alkali metal hydroxide. The excess alcohol both helps complete the reaction of the alkali metal hydroxide and forms the azeotrope necessary for the azeotropic removal of water from the reaction zone.

The alkali metal hydroxide may be sodium, potassium or lithium hydroxide; sodium hydroxide is preferred for economic reasons. The hydroxides are continuously fed to the reaction column as aqueous solutions and are fairly concentrated to reduce the amount of water which must be azeotropically removed from the system. Typically, sodium hydroxide is fed to the column as a 50% by weight solution.

The feed rate of the vaporized alcohol and the alkali metal hydroxide solutions are easily adjusted to and controlled for the size of the equipment employed. Similarly, the reaction temperature in the column is controlled by the azeotroping temperature and the amount of alkoxide in the reaction column. For example when a 50% solution of sodium hydroxide is continuously fed into the column along with vaporized 2-butoxyethanol the midpoint of the column is maintained at 120° C.

The present process will be described with reference to the figure and the manufacture of sodium butoxide. Sodium hydroxide (50% by weight aqueous solution) is continuously removed from storage tank T-6 by pump P-1 and continuously fed through line L-14 to the column reactor D-1 at the rate of 8–12 pounds per minute on a 100% sodium hydroxide basis. N-butanol is removed from tank T-1 by pump P-5 and fed through line L-15 to interchanger H-2 where it cools hot alkoxide on its way to alkoxide storage tank T-2. The warmed n-butanol leaves the alkoxide/alcohol interchanger H-2 through line L-1 and enters alcohol flash vessel T-5. Pump P-3 removes N-butanol from the bottom of vessel T-5 and circulates the N-butanol through steam heated alcohol flash vessel reboiler H-4 where the N-butanol is vaporized. The vaporized N-butanol is returned to the top of vessel T-5. Vaporized N-butanol exits vessel T-5 and proceeds to lines L-3 and L-5 to a lower portion of column reactor D-1. The midcolumn temperature of column reactor D-1 is maintained at 110° C. to 150° C. by varying the sodium hydroxide feed rate and/or varying the pressure in the vessel T-5. There is excess N-butanol in the system and this excess alcohol forms an azeotrope with the water in the aqueous sodium hydroxide feed solution and the water formed by the reaction to form the alkoxide. The azeotrope leaves the column reactor through line L-16 and is condensed in water cooled column reactor condenser H-1. The condensate goes through the line L-8 to decanter vessel T-3 where the alcohol and water are separated into two phases. The water is removed from the process through line L-10. Alcohol is removed from vessel T-3 and recycled through line L-9 to the column reactor D-1. The product alkoxide leaves the column reactor D-1 through line L-11. The underflow from the column reactor is pumped by pump P-4 to steam heated alkoxide concentrating vessel heater H-3 and thence through line L-7 to vessel T-4 where excess alcohol is vaporized and recycled to the column reactor D-1. The alkoxide product leaves the vessel T-4 through line L-6 and passes through interchanger H-3 on way to line L-13 and product storage vessel T-2.

The process is similarly conducted when the alcohol is 2-butoxyethanol and the product is sodium 2-butoxy ethoxide. However, when making this product the vessel T-4 may be isolated from the process configuration and not used. In this instance the column reactor underflow goes from pump P-4 through line L-12 through interchanger H-2 and thence through line L-13 storage. When making sodium 2-butoxyethoxide the column midpoint is maintained at about 168°–172°P0 C. Utilization of the vessel T-4 alkoxide concentrator loop is useful in producing a concentrated alkoxide product. However, the boiling points of the higher molecular weight alcohols are such that normally available plant process steam may not provide sufficient heat for this operation; however, hot oil or some other high temperature heat exchange material may be effective so that this option may be used to make a more concentrated alkoxide.

This invention is further illustrated by the following examples. The equipment configuration in the examples is as shown in the figure and the operation is as described above. The first three examples produce 2-butoxyethoxide, and, as described above, the equipment in the vessel T-4 loop was not employed. All reactions were conducted in a nitrogen atmosphere. Pressure was measured in inches of water at 60° F. (15.6° C.).

EXAMPLE 1

Air was purged from the unit with nitrogen and a nitrogen atmosphere was maintained at all times. Sodium hydroxide, as a 50% aqueous solution was fed to the column reactor at a rate of 4.58 kg per minute based on 100% sodium hydroxide. The pressure in the vessel T-5 was maintained at 14.33 kPa (16° C.) and a temperature of 177° C. The mid-column temperature of the column reactor D-1 under these conditions was 134° C. while operating continuously the alkoxide underflow assayed 29% 2-butoxyethoxide and the unreacted sodium hydroxide in the underflow was 0.044% by weight. Tributoxyethyl phosphate ester made from the alkoxide had a commercially acceptable color.

EXAMPLE 2

The process of Example 1 was followed except that the vessel T-5 temperature was maintained at 175° C. and under pressure of 19.41 kPa. With a sodium hydroxide feed rate on a 100% basis (50% aqueous by weight) fed at 4.63 kg per hour the column reactor D-1 mid-column temperature was 141° C. The underflow assayed 32% 2-butoxyethoxide and had unreacted sodium hydroxide content of 0.130%. Tributoxyethyl phosphate made from the alkoxide had a commercially acceptable color.

EXAMPLE 3

The process of Example 1 using 2-butoxyethanol feed to make 2-butoxyethoxide was repeated with maintaining T-5 vessel pressure of 19.2 kPa and a temperature of 179° C. With a feed rate of 50% sodium hydroxide of 4.03 kg per minute on a 100% unreacted sodium hydroxide content of 0.113%. Tributoxyethyl phosphate made from the alkoxide had a commercially acceptable color.

EXAMPLE 4

The unit as described above and shown in the figure was cleaned and charged with N-butanol. In this example the T-4 configuration was used. The unit was started up using a sodium hydroxide feed rate of 3.67 kg per minute on a 100% basis of a 50% aqueous sodium hydroxide solution the vessel T-5 pressure was maintained at 39.8 kPa and a temperature of 129° C. The temperature in the T-4 vessel was maintained at 170° C. These operating conditions produced a mid-column temperature in the column reactor of 116° C. The underflow assayed 13% alkoxide from the underflow from column D-1 and an unreacted sodium hydroxide content of 0.065% while the underflow from the T-4 concentrator assayed 25% sodium butoxide and had an unreacted sodium hydroxide content of 0.083%. Tributylphosphate ester made from the butoxide had a commercially acceptable color.

EXAMPLE 5

The process of Example 4 was repeated using N-butanol feed and producing sodium butoxide. In this example the vessel T-5 pressure was maintained at 40.1 kPa and a temperature of 129° C. The T-4 unit temperature was maintained at 170° C. Using a sodium hydroxide feed rate of 3.72 kg per minute (100% basis) of a 50% aqueous sodium hydroxide solution the mid-column temperature of the column reactor D-1 was 115° C. The assay of the column reactor D-1 underflow was 14% alkoxide and contained 0.057% unreacted sodium hydroxide. The underflow from the T-4 concentrator assayed 25% sodium butoxide and contained 0.062% unreacted sodium hydroxide. Tributylphosphate ester made from the butoxide had a commercially acceptable color.

EXAMPLE 6

The process of Example 4 was again repeated under the following conditions: The vessel T-5 was operated at a pressure of 36.6 kPa and a temperature of 132° C. The T-4 concentrator temperature was maintained at 172° C. and the sodium hydroxide feed rate to the column reactor was 3.72 kg per minute on a 100% basis of a 50% sodium hydroxide aqueous solution. These conditions produced a mid-column temperature in the column reactor of 118° C. The underflow from the column reactor D-1 assayed 15% alkoxide and contained 0.080% unreacted sodium hydroxide. The underflow from the T-4 concentrator assayed 27% sodium butoxide and contained 0.067% unreacted sodium hydroxide. Tributylphosphate ester made from the butoxide had a commercially acceptable color.

COMPARISON EXAMPLE

The process of Example 1 was repeated except that the alcohol from vessel T-3 was diverted from the column D-1 to the alcohol recovery section of a phosphate ester plant that utilized the alkoxide product to make tributoxyethyl phosphate. The phosphate ester is produced in the presence of excess 2-butoxyethanol which is recovered after the phosphate ester reaction mixture is washed with water to remove sodium chloride. The wet alcohol from the T-3 separator and the wet alcohol recovered from the phosphate ester plant were combined and the water removed by distillation. The dried alcohol was returned to column D-1. 2-Butoxyethoxide made fom this alcohol was subsequently used to make tributoxyethyl phosphate. Surprisingly this tributoxyethyl phosphate ester was severely discolored; it had an ASTM D1544-80 color of 13. 2-Butoxyethanol samples recovered from the alcohol drier in the phosphate ester plant were found to be discolored. It was surprising that drying the alcohol from the T-3 separator and returning it to the D-1 reactor would cause the alcohol and phosphate ester product to be severely discolored.

The conventional batch process for producing aliphatic phosphate esters disclosed in U.S. Pat. No. 3,020,303 employs an azeotropic agent such as benzene, heptane or naphtha to remove water from the alkoxidation reaction mixture. Heptane, a preferred azeotropic agent forms an azeotrope containing about 13% water. An advantage of the present invention is that heptane is not necessary; for example, when 2-butoxyethanol is used in the reaction this alcohol forms an azeotrope that is about 80% water. This results in a twofold benefit: (1) eliminating the expense of having and handling the heptane and more importantly, (2) much less energy is used in removing the same weight of water from the system; only 1/30th of the weight of organic material is recycled to the column. The yields of the present process are improved by the more complete reaction of the hydroxide. Finally, productivity is improved by eliminating downtime between batches required to remove residue from the batch reactor, clean and recharge the reactor and time spent transferring products from the production area of the plant to the product refining area, etc.

We claim:

1. A continuous process for producing alkali metal alkoxides comprising the steps:
    (a) Continuously introducing an aqueous solution of an alkali metal hydroxide into an upper section of a column-reactor;
    (b) Continuously vaporizing an aliphatic alcohol of the formula

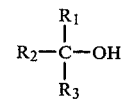

in which $R_1$, $R_2$ and $R_3$ are selected from hydrogen, alkyl or alkoxyalkyl radicals, said aliphatic alcohol having 4 to 18 carbon atoms, and feeding the vaporized alcohol into a lower section of the column reactor at a rate of 2 to 4 moles of alcohol per mole of alkali metal hydroxide introduced into the column reactor;
    (c) Reacting the aliphatic alcohol with the alkali metal hydroxide in the column reactor;
    (d) Concurrently removing water from the alkali metal hydroxide solution and the alkoxide formation from an upper section of the column reactor in the form of an azeotrope;
    (e) Continuously condensing and separating the azeotrope into an alcohol phase and a water phase, the water phase being removed from the process and the alcohol phase being returned to the column reactor;
    (f) Recovering a substantially anhydrous reaction product comprising alkoxide product and aliphatic alcohol from a lower section of the column reactor while simultaneously maintaining a non-oxidizing atmosphere throughout the conduct of steps a through f.

2. The process of claim 1 wherein the aliphatic alcohol is selected from alkanols of the formula R—OH in which R contains 4 to 12 carbon atoms and alkoxy alkanols of the formula $R_4$—O—$R_5$—OH in which $R_4$ contains 1 to 6 carbon atoms and $R_5$ contains 1 to 4 carbon atoms.

3. The process of claim 1 wherein the alkali metal hydroxide is selected from sodium hydroxide, potassium hydroxide and lithium hydroxide.

4. The process of claim 1 wherein the reaction product removed from a lower section of the column reactor is distilled to recover part of the unreacted alcohol which is returned to the column reactor.

5. The process of claim 2 wherein the aliphatic alcohol is butanol.

6. The process of claim 2 wherein the aliphatic alcohol is 2-butoxyethanol.

* * * * *